(12) United States Patent
Wiemer et al.

(10) Patent No.: US 7,268,124 B2
(45) Date of Patent: Sep. 11, 2007

(54) GERANYLGERANYL PYROPHOSPHATE SYNTHASE INHIBITORS

(75) Inventors: David F. Wiemer, Iowa City, IA (US); Raymond J. Hohl, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/212,128

(22) Filed: Aug. 25, 2005

(65) Prior Publication Data

US 2006/0052347 A1 Mar. 9, 2006

Related U.S. Application Data

(60) Provisional application No. 60/604,309, filed on Aug. 25, 2004.

(51) Int. Cl.
  *A01N 57/00* (2006.01)
  *A61K 31/675* (2006.01)
(52) U.S. Cl. .................. 514/89; 514/102; 514/90; 514/91; 544/57; 544/157; 546/22; 548/413
(58) Field of Classification Search ............ 514/89, 514/102, 90, 91; 544/157, 57; 546/22; 548/413
  See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,774,262 A | 9/1988 | Blanquet et al. | |
| 4,820,508 A | 4/1989 | Wortzman et al. | |
| 4,938,949 A | 7/1990 | Borch et al. | |
| 4,992,478 A | 2/1991 | Geria et al. | |
| 5,583,122 A | 12/1996 | Benedict et al. | |
| 6,727,234 B2 | 4/2004 | Wiemer et al. | |
| 2004/0167102 A1 | 8/2004 | Wiemer et al. | |

OTHER PUBLICATIONS

Cohen et al., Inhibition of human smooth muscle cell proliferation in culture by farnesyl pyrophosphate analogues, inhibitors of in vitro protein: farnesyl transferase, Biochemical Pharmacology, vol. 57, pp. 365-373, 1999.*

Muehlbauer et al., Effect of various Polyphosphonates on ectopic Calcification and Bone Resorption in Rats, Mineral and Electrolyte Metabolism, 1981, 5 (6), 296-303.*

Cohen et al., {Inhibition of human smooth muscle cell proliferation in culture by farnesyl pyrophosphate analogues, inhibitors of in vitro protein: farnesyl transferase, Biochemical Pharmacology, vol. 57, pp. 365-373, 1999}.*

Muehlbauer et al., {Effect of various Polyphosphonates on ectopic Calcification and Bone Resorption in Rats, Mineral and Electrolyte Metabolism, 1981, 5 (6), 296-303}.*

(Continued)

*Primary Examiner*—Thurman K. Page
*Assistant Examiner*—Chukwuma Nwaonicha
(74) *Attorney, Agent, or Firm*—Viksnins Harris & Padys PLLP

(57) ABSTRACT

The invention provides novel pyrophosphate synthase inhibitors of formula I as well as compositions comprising such inhibitors and methods for their use.

57 Claims, 2 Drawing Sheets

OTHER PUBLICATIONS

Cohen, L. H. et al., "Inhibition of human smooth muscle cell proliferation in culture by farnesyl pyrophosphate analogues, inhibitors of in vitro protein: Farnesyl transferase" *Biochemical Pharmacology*, vol. 57, No. 4, 365-474, 1999.

Fairlamb, I J S et al., "Cycloisomerisation of modified terpenoid 1,6-enynes-synthesis of conformationally-restricted cyclic farnesyl analogues", *Tetrahedron Letters*, vol. 43, No. 30, 5327-5331, 2002.

Hutchinson, D. W. et al., "Synthesis of alkylated methylene bisphosphonates via organothallium intermediates", *Journal of Organometallic Chemistry*, vol. 291, No. 2, 145-151, 1985.

Muehlbauer, R. C. et al., "Effect of various polyphosphonates on ectopic calcification and bone resorption in rats", *Mineral and Electrolyte Metabolism*, vol. 5, No. 6, 296-303, 1981.

Quimby, O. T. et al., "Metalated methylenediphosphate esters. Preparation characterisation and synthetic applications", *Journal of Organometallic Chemistry*, vol. 291, No. 2, 145-151, 1968.

Valentijn, A. R. P. M. et al., "Synthesis of Pyrophosphonic Acid Analogues of Farnesyl Pyrophosphate", *Tetrahedron*, vol. 51, No. 7, 2099-2108, 1995.

International PCT Search Report for PCT/US2005/030304, (2006).

Armstrong et al. "cDNA cloning and expression of the alpha and beta subunits of rat Rab geranylgeranyl transferase." *J. Biol. Chem.* 268: 12221—12229 (1993)

Benford et al. "Farnesol and geranylgeraniol prevent activation of caspases by aminobisphosphonates: biochemical evidence for two distinct pharmacological classes of bisphosphonate drugs." *Mol Pharmacol.* 56(1):131-140 (1999).

Bergstrom et al. "Alendronate is a specific, nanomolar inhibitor of farnesyl diphosphate synthase." *Arch Biochem Biophys.* 373(1):231-241 (2000).

Ebetino et al. "Recent Work on the Synthesis of Phosphonate-containing, Bone-active Heterocyles" *Heterocycles* 30:855-862 (1990).

Ericsson et al. "Distribution of prenyltransferases in rat tissues," *J. Biol. Chem.* 268: 832-838 (1993).

Ericsson et al. "Human geranylgeranyl diphosphate synthase: isolation of the cDNA, chromosomal mapping and tissue expression." *J. Lipid Res.* 39(9):1731-1739 (1998).

Fisher et al. "Alendronate mechanism of action: geranylgeraniol, an intermediate in the mevalonate pathway, prevents inhibition of osteoclast formation, bone resorption, and kinase activation in vitro." *PNAS,* 96(1):133-138 (1999).

Fuse et al. "Regulation of geranylgeranyl pyrophosphate synthase in the proliferation of rat FRTL-5 cells: involvement of both cAMP-PKA and PI3-AKT pathways," *Biochem Biophys Res Commun.* 315(4):1147-1153 (2004).

Holstein et al. "Consequences of Mevalonate Depletion." *J. Biol. Chem.* 277:10678-10682 (2002).

Holstein et al. "Isoprenoid pyrophosphate analogues regulate expression of Ras-related proteins." *Biochemistry* 42(15): 4384-4391 (2003).

Holstein et al. "Isoprenoids influence expression of Ras and Ras-related proteins." *Biochemistry* 41:13698-13704 (2002).

Holstein et al. "Phosphonate and bisphosphonate analogues of farnesyl pyrophosphate as potential inhibitors of farnesyl protein transferase." *Bioorg Med Chem.* 6(6):6876-94 (1998).

Keller et al. "Mechanism of aminobisphosphonate action: characterization of alendronate inhibition of the isoprenoid pathway." *Biochem Biophys Res Commun.* 266:560-563 (1999).

Luckman et al. "Nitrogen-containing bisphosphonates inhibit the mevalonate pathway and prevent post-translational prenylation of GTP-binding proteins, including Ras." *J. Bone Miner. Res.* 13(4):581-589 (1998).

Martin et al. "Bisphosphonates inhibit the growth of *Trypanosoma brucei, Trypanosoma cruzi, Leishmania donovani, Toxoplasma gondii,* and *Plasmodium faiciparum*: a potential route to chemotherapy." *J. Med. Chem.* 44(6):909-916 (2001).

McKenna et al. "The facile dealkylation of phosphonic acid dialkyl esters by bromotrimethylsilane." *Tetrahedron Lett.* 18:155-158 (1977).

Moomaw et al. "Mammalian protein geranylgeranyltransferase. Subunit composition and metal requirements." *J. Biol. Chem.* 267:17438-17443 (1992).

Reiss et al. "Inhibition of purified p21ras farnesyl:protein transferase by Cys-AAX tetrapeptides." *Cell* 62(1):81-8 (1990).

Reszka et al. "Bisphosphonates Act Directly on the Osteoclast to Induce Caspase Cleavage of Mst1 Kinase during Apoptosis." *J. Biol. Chem.* 274:34967-34973 (1999).

Sagami et al. "Studies on geranylgeranyl diphosphate synthase from rat liver: specific inhibition by 3-azageranylgeranyl diphosphate." *Arch Biochem Biophys.* 297(2):314-320 (1992).

Shull et al., "Synthesis and biological activity of isoprenoid bisphosphonates", *Bioorg Med Chem.*, 14(12), 4130-4136 (2006).

Spear et al. "Molecular cloning and promoter analysis of the rat liver farnesyl diphosphate synthase gene." *J. Biol. Chem.* 267: 14462-14469 (1992).

Szabo et al. "Inhibition of geranylgeranyl diphosphate synthase by bisphosphonates and diphosphates: a potential route to new bone antiresorption and antiparasitic agents." *J Med Chem.* 45(11):2185-2196 (2002).

van Beek et al. "Farnesyl pyrophosphate synthase is the molecular target of nitrogen-containing bisphosphonates." *Biochem Biophys Res Commun.* 264(1):108-111 (1999).

van Beek et al. "The role of geranylgeranylation in bone resorption and its suppression by bisphosphonates in fetal bone explants in vitro: A clue to the mechanism of action of nitrogen-containing bisphosphonates." *J Bone Miner Res.* 14(5):722-729 (1999).

Vepsäläinen et al. "Bisphosphonate prodrugs: a new synthetic strategy to tetraacyloxymethyl esters of methylenebisphosphonates." *Tetrahedron. Lett.* 40:8491-8493 (1999).

Vicent et al. "The Branch Point Enzyme of the Mevalonate Pathway for Protein Prenylation Is Overexpressed in the *ob/ob* Mouse and Induced by Adipogenesis." *Mol. Cellular Biol.* 20:2158-2166 (2000).

Virtanen et al. "Alendronate inhibits invasion of PC-3 prostate cancer cells by affecting the mevalonate pathway," *Cancer Res.* 62(9):2708-2714 (2002).

Xing et al. "Lovastatin is antiarrhythmic in ischemic heart tissue by blocking triggered activity." *J. of Invest. Med.* 53(2):S368 (2005).

Yokoyama et al. "Purification of a mammalian protein geranylgeranyltransferase. Formation and catalytic properties of an enzyme-geranylgeranyl pyrophosphate complex." *J Biol Chem.* 268(6):4055-4060 (1993).

Zenitani et al. "Gerfelin, a novel inhibitor of geranylgeranyl diphosphate synthase from *Beauveria felina* QN22047. I. Taxonomy, fermentation, isolation, and biological activities." *J Antibiot* (Tokyo). 56(7):617-621 (2003).

\* cited by examiner

GERANYLGERANYL PYROPHOSPHATE SYNTHASE INHIBITORS

RELATED APPLICATION

This patent document claims the benefit of priority of U.S. application Ser. No. 60/604309, filed Aug. 25, 2004, which application is herein incorporated by reference.

BACKGROUND

Farnesyl pyrophosphate (FPP) and geranylgeranyl pyrophosphate (GGPP) are branch-point intermediates in the isoprenoid biosynthetic pathway. These isoprenoids are synthesized via a series of sequential condensations of five-carbon units catalyzed by the enzymes FPP synthase and GGPP synthase, respectively. FPP sits at the branch-point between sterol and longer chain non-sterol synthesis. GGPP is a precursor for ubiquinone synthesis and in plants, serves as the precursor for carotenoids, diterpenes, and chlorophylls. FPP and GGPP also serve as isoprene donors in the isoprenylation of proteins catalyzed by the enzymes farnesyl protein transferase (FPTase) and geranylgeranyl protein transferase (GGPTase) I and II (See Reiss, Y., et al., *Cell.* 1990, 62, 81-88; Moomaw, J. F. and Casey, P. J., *J. Biol. Chem,* 1992, 267, 17438-17443; Yokoyama, K. and Gelb, M. H., *J. Biol. Chem,* 1993, 268, 4055-4060; and Armstrong, S. A., et al., *J. Biol. Chem.,* 1993, 268, 2221-12229). Isoprenylation of proteins, in particular small GTPases, serves to ensure proper intracellular localization and function.

While expression of FPP synthase has been shown to be regulated by sterol availability (Spear, D. H., et al., *J. Biol. Chem,* 1992, 267, 14462-14469), GGPP synthase appears to be regulated in a sterol-independent manner. The gene encoding human GGPP synthase has been cloned and GGPP synthase mRNA is expressed ubiquitously, with highest levels found in the testis (Ericsson, J., et al., *J. Lipid Res,* 1998, 39, 1731-1739). In rat thyroid cells, GGPP synthase expression is upregulated, coincident with cellular proliferation, following the stimulation of cells with thyrotropin and insulin (Fuse, M., et al., *Biochem. Biophys. Res. Commun.,* 2004, 315, 1147-1153). In addition, GGPP synthase was first cloned in mice as a result of its identification as one of the genes upregulated in ob/ob mice, a model of obesity and insulin resistance (Vicent, D., et al., *Mol. Cellular Biol,* 2000, 20, 2158-2166). Thus alterations in levels of GGPP appears important in both physiological and pathophysiological processes and a method to experimentally manipulate intracellular GGPP levels would provide further understanding of these processes.

Nitrogen-containing bisphosphonates, including alendronate, pamidronate, and zoledronic acid, have been shown to inhibit FPP synthase (van Beek, E., et al., *Biochem. Biophys. Res. Commun.,* 1999, 264, 108-111; Keller, R. K. and Fliesler, *Biochem. Biophys. Res. Commun.,* 1999, 266, 560-563; and Bergstrom, J. D., Bostedor, R. G., et al., *Arch. Biochem. Biophys.,* 2000, 373, 231-241). This class of drugs is used to inhibit bone resorption in a number of diseases, including osteoporosis, tumor-associated bone disease, and Paget's disease. The aminobisphosphonates, by depleting cells of both FPP and GGPP, prevent the farnesylation and geranylgeranylation of small GTPases (Luckman, S. P., Hughes, D. E., et al., *J. Bone Miner. Res.,* 1998, 13, 581-589; Reszka, A. A., Halasy-Nagy, et al., *J. Biol. Chem.,* 1999, 274, 34967-34973; and Benford, H. L., Frith, J. C., et al., *Mol. Pharmacol.,* 1999, 56, 131-140). It appears that the depletion of GGPP, with subsequent prevention of geranylgeranylation is the critical mechanism underlying the effects of the aminobisphosphonates. In specific, it has been suggested that the loss of activity of geranylgeranylated proteins, such as cdc42, Rac, and Rho in osteoclasts, is directly related to the antiresorptive effects as restoration of geranylgeranylation blocks the effects of the aminobisphosphonates on osteoclasts (Reszka, A. A., Halasy-Nagy, et al., *J. Biol. Chem.,* 1999, 274, 34967-34973; Fisher, J. E., Rogers, M. J., et al., *Proc. Nat. Acad. Sci. U.S.A.,* 1999, 96, 133-138; and van beek, E., Lowik, et al., *J. Bone Miner. Res.,* 1999, 14, 722-729). The bisphosphonates may have additional therapeutic uses as it was recently demonstrated that alendronate inhibits the invasion of both prostate and breast cancer cells (Virtanen, S. S., Vaananen, H. K., et al., *Cancer Res.,* 2002, 62, 2708-2714). Finally, a number of nitrogen-containing bisphosphonates have also been shown to inhibit the growth of parasites, including *Trypanosoma brucei, Leishmania donovani,* and *Plasmodium falciparum* (Martin, M. B., Grimley, J. S., et al., *J. Med. Chem.,* 2001, 44, 909-916).

There are no GGPP synthase inhibitors currently available for clinical use. There have been several reports of compounds, both synthetic and natural, which inhibit GGPP synthase (Sagami, H., Korenaga, T., et al., *Arch. Biochem. Biophys.,* 1992, 297, 314-320; Szabo, C. M., Matsumura, Y., et al., *J. Med. Chem.,* 2002, 45, 2185-2196; and Zenitani, S., Tashiro, S., et al., *J. Antibiot.* (*Tokyo*)., 2003, 56, 617-621). The potency and selectivity of these compounds for GGPP synthase vs. FPP synthase varies significantly. Given the findings discussed above, there is considerable interest in the development of specific GGPP synthase inhibitors.

It would be predicted that selective GGPP synthase inhibitors could be used for the same therapeutic applications as FPP synthase inhibitors as novel anticancer agents, with the added advantage of more specifically affecting the essential downstream targets. That is, while levels of GGPP would be depleted, synthesis of FPP would not be affected, hence the pathways utilizing FPP (e.g., sterol synthesis, dolichol synthesis) would be preserved.

GGPP synthase inhibitors would also serve as important tools which could be used in studies addressing the significance of isoprenoid intermediate pool size, flux through the isoprenoid biosynthetic pathway, hierarchy among geranylgeranylated proteins, and regulatory properties of endogenous isoprenoid pyrophosphates. In specific, while both FPP and GGPP have been shown to regulate the expression of a number of small GTPases (Holstein, S. A., Wohlford-Lenane, C. L. et al., *J. Biol. Chem.,* 2002, 277, 10678-10682; Holstein, S. A., Wohlford-Lenane, C. L. and Hohl, *Biochemistry,* 2002, 41, 13698-13704; and Holstein, S. A., Wohlford-Lenane, C. L., et al., *Biochemistry,* 2003, 42, 4384-4391), the relative contribution of the two isoprenoid species has yet to be fully determined. Thus the availability of GGPP synthase inhibitors would provide for novel experimental approaches and improved therapeutic strategies.

In summary there is currently a need for GGPP synthase inhibitors. Such compounds would be useful as chemical tools to ascertain the importance of GGPP in a number of cellular processes. Additionally, they would be anticipated to be useful 1) as antiproliferative agents for the treatment of cancer (based on the FPTase inhibitors), 2) to inhibit testicular function and thus have activity to decrease male fertility (based on high levels in testes), and 3) to treat insulin resistance and obesity based on the ob/ob mouse model of insulin resistance and obesity. They would also be anticipated to be useful in the treatment of a number of parasitic diseases and to have potent osteoclast inhibitory function and to be useful in the prevention and treatment of osteoporosis.

SUMMARY OF CERTAIN EMBODIMENTS OF THE INVENTION

The present invention provides compounds that act as GGPP synthase inhibitors. Accordingly there is provided a compound of the invention which is a compound of formula I:

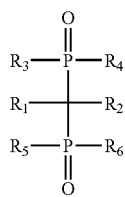

wherein:

$R_1$ is a saturated or unsaturated ($C_5$-$C_{20}$)alkyl chain that optionally comprises one or more aryl rings in the chain and that is optionally substituted with one or more halo, trifluoromethyl, —$OR_a$, —P(=O)($OR_a$)$_2$, or —$NR_bR_c$;

$R_2$ is a saturated or unsaturated ($C_5$-$C_{20}$)alkyl chain that optionally comprises one or more aryl rings in the chain and that is optionally substituted with one or more halo, trifluoromethyl, —$OR_a$, —P(=O)($OR_a$)$_2$, or —$NR_bR_c$;

each $R_3$, $R_4$, $R_5$, and $R_6$ is independently OH or ($C_1$-$C_6$) alkoxy;

each $R_a$ is independently H, ($C_1$-$C_6$)alkyl, or aryl; and each $R_b$ and $R_c$ is independently H, ($C_1$-$C_6$)alkyl, or aryl; or $R_b$ and $R_c$ together with the nitrogen to which they are attached form a pyrrolidino, piperidino, morpholino, or thiomorpholino ring;

wherein any aryl is optionally substituted with one or more (e.g. 1, 2, 3, or 4) ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or S(O)$_2NR_dR_e$, wherein each $R_d$ and $R_e$ is independently H or ($C_1$-$C_6$)alkyl;

or a pharmaceutically acceptable salt or prodrug thereof.

Also provided is a compound of the invention that includes or that is linked to one or more detectable groups. In some embodiments of the invention, at least one of the one or more detectable groups is a fluorescent group. In some embodiments of the invention, at least one of the one or more detectable groups is a radionuclide.

The invention also provides a pharmaceutical composition comprising a compound of the invention and a pharmaceutically acceptable diluent or carrier.

The invention also provides a method for inhibiting geranylgeranyl pyrophosphate synthase comprising contacting the geranylgeranyl pyrophosphate synthase in vitro or in vivo with an effective inhibitory amount of a compound of the invention.

The invention also provides a method for treating cancer comprising administering to an animal (e.g. a mammal such as a human) in need of such treatment an effective amount of a compound of the invention.

The invention also provides a method for modulating (e.g., increasing or decreasing) testicular function comprising administering to an animal (e.g. a mammal such as a human) in need of such treatment an effective amount of a compound of the invention.

The invention also provides a method for modulating (e.g., increasing or decreasing) fertility comprising administering to an animal(e.g. a mammal such as a human) in need of such treatment an effective amount of a compound of the invention.

The invention also provides a method for treating insulin resistance comprising administering to an animal (e.g. a mammal such as a human) in need of such treatment an effective amount of a compound of the invention.

The invention also provides a method for treating obesity comprising administering to an animal (e.g. a mammal such as a human) in need of such treatment an effective amount of a compound of the invention.

The invention also provides a method for modulating (e.g., increasing or decreasing) weight gain comprising administering to an animal (e.g. a mammal such as a human) in need of such treatment an effective amount of a compound of the invention.

The invention also provides a method for modulating (e.g., increasing or decreasing) osteoclast function comprising administering to an animal (e.g. a mammal such as a human) in need of such treatment an effective amount of a compound of the invention.

The invention also provides a method for treating a parasitic infection comprising administering to an animal (e.g. a mammal such as a human) in need of such treatment an effective amount of a compound of the invention.

The invention also provides a method for producing an antiparasitic effect comprising contacting a parasite in vitro or in vivo with an effective amount of a compound of the invention.

The invention also provides a compound of the invention for use in medical treatment or diagnosis.

The invention also provides a method for imaging a tissue including contacting the tissue with an effective amount of a compound of the invention and detecting the compound so as to image the tissue.

The invention also provides a method for treating cardiac arrhythmia including administering to an animal (e.g. a mammal such as a human) in need of such treatment an effective amount of a compound of the invention.

The invention also provides the use of a compound of the invention to prepare a medicament useful for treating cardiac arrhythmia in an animal (e.g. a mammal such as a human).

The invention also provides the use of a compound a compound of the invention to prepare a medicament useful for treating cancer in an animal (e.g. a mammal such as a human).

The invention also provides the use of a compound of the invention to prepare a medicament useful for modulating (e.g., increasing or decreasing) testicular function in an animal (e.g. a mammal such as a human).

The invention also provides the use of a compound a compound of the invention to prepare a medicament useful for modulating (e.g., increasing or decreasing) fertility in an animal (e.g. a mammal such as a human).

The invention also provides the use of a compound a compound of the invention to prepare a medicament useful for treating insulin resistance in an animal (e.g. a mammal such as a human).

The invention also provides the use of a compound of the invention to prepare a medicament useful for treating obesity in an animal (e.g. a mammal such as a human).

The invention also provides the use of a compound of the invention to prepare a medicament useful for modulating (e.g., increasing or decreasing) weight gain in an animal (e.g. a mammal such as a human).

The invention also provides the use of a compound of the invention to prepare a medicament useful for modulating (e.g., increasing or decreasing) osteoclast function in an animal (e.g. a mammal such as a human).

The invention also provides the use of a compound of the invention to prepare a medicament useful for treating a parasitic infection in an animal (e.g. a mammal such as a human).

The invention also provides processes and intermediated disclosed herein that are useful for preparing compounds of formula (I) or salts or prodrugs thereof.

DETAILED DESCRIPTION

Figure 1:
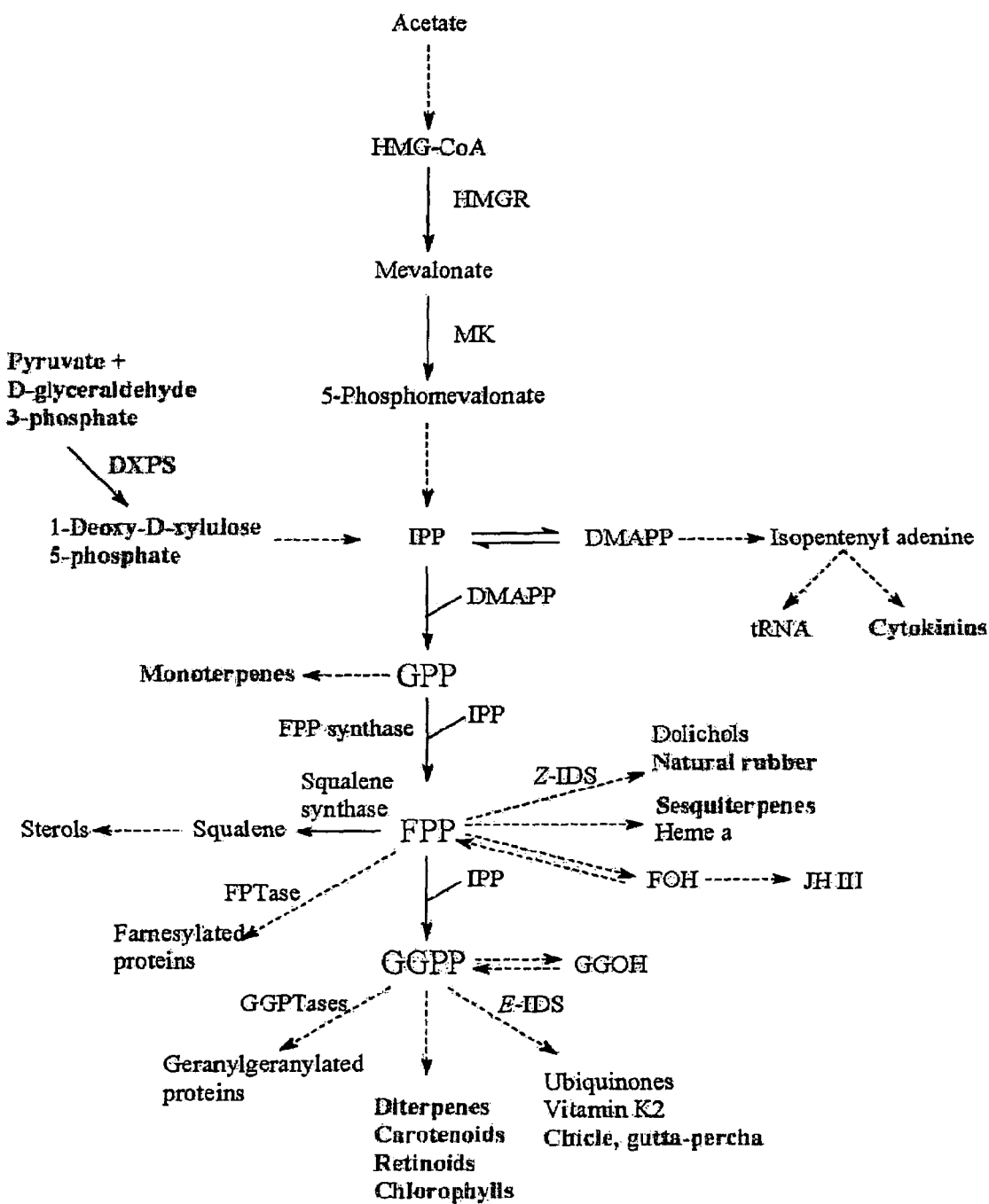
FIG. 1 illustrates the actions of farnesyl pyrophosphate and geranylgeranyl pyrophosphate in the isoprenoid biosynthetic pathway.
Figure 2:
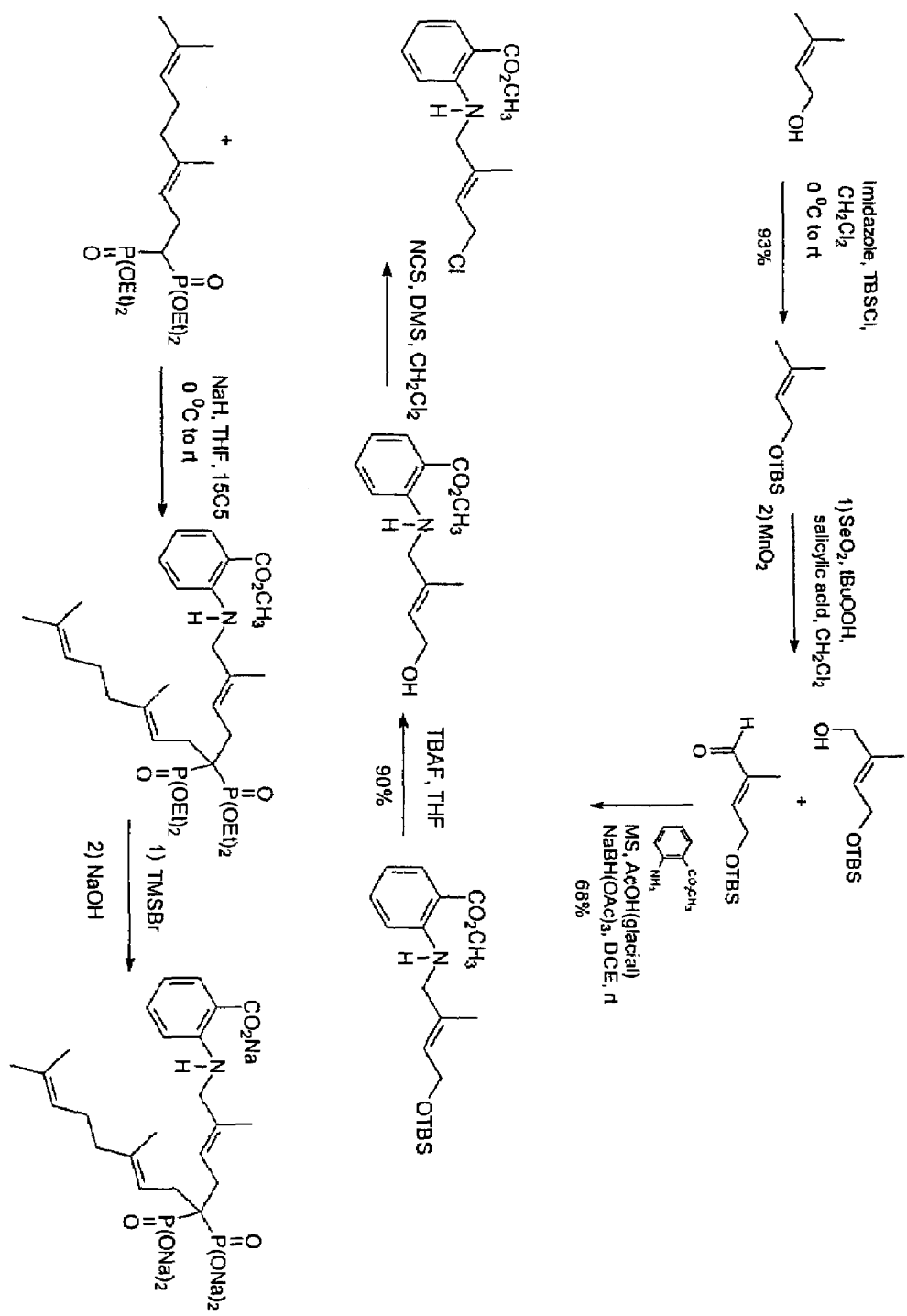
FIG. 2 illustrates the synthetic sequence used to prepare bisphosphonate 15.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). An amino acid can be linked to the remainder of a compound of formula I through the carboxy terminus, the amino terminus, or through any other convenient point of attachment, such as, for example, through the sulfur of a cysteine. In one embodiment of the invention, when an amino acid is linked to a phosphorous in a compound of formula I, the amino acid is linked through the amino terminus or through another nitrogen of the amino acid.

The term "prodrug" is well understood in the art and includes compounds that are converted to pharmaceutically active compounds in vivo (e.g. in an animal such as a mammal). For example, see Remington's Pharmaceutical Sciences, 1980, vol. 16, Mack Publishing Company, Easton, Pa., 61 and 424. In particular, a number of groups suitable for preparing prodrug forms of phosphorous containing compounds (e.g. phosphonates) are known. For example, see Galmarini C M, et al., International Journal of Cancer, 2003, 107 (1), 149-154; Wagner, C. R., et al., Medicinal Research Reviews, 2000, 20, 417-51; McGuigan, C., et al., Antiviral Research, 1992, 17, 311-321; and Chapman, H., et al., Nucleosides, Nucleotides & Nucleic Acids, 2001, 20, 1085-1090. The invention includes phosphonate prodrug analogs prepared from suitable in vivo hydrolysable groups.

It will be appreciated by those skilled in the art that compounds of the invention having a chiral center may exist in and be isolated in optically active and racemic forms. For example, it is possible for one or both phosphorous atoms in a compound of formula I to be chiral centers. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine enzyme inhibitory activity using the standard tests that are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; and aryl can be phenyl, indenyl, or naphthyl.

A specific value for $R_1$ is a saturated or unsaturated $(C_5-C_{20})$alkyl chain.

Another specific value for $R_1$ is an unsaturated $(C_5-C_{20})$ alkyl chain.

Another specific value for $R_1$ is a saturated or unsaturated $(C_5-C_{20})$alkyl chain that comprises one or more aryl rings in the chain.

Another specific value for $R_1$ is a saturated or unsaturated $(C_5-C_{20})$alkyl chain that is substituted with one or more halo, trifluoromethyl, $OR_a$ or $NR_bR_c$.

Another specific value for $R_1$ is the formula,

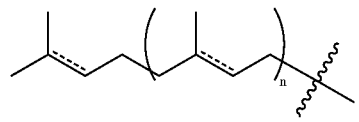

wherein n is 0, 1, 2, or 3; and each bond designated by - - - is independently either present or is absent. A specific value for n is 0.

Another specific value for n is 1.

Another specific value for n is 2.
Another specific value for n is 3.
Another specific value for $R_1$ is the formula,

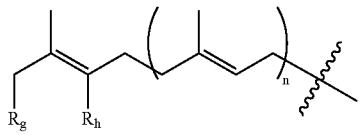

wherein:
n is 0, 1, 2, or 3; and
$R_g$ and $R_h$ together with the atoms to which they are attached form an aryl ring that is optionally substituted with one or more (e.g. 1, 2, 3, or 4) ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or ($C_1$-$C_6$)alkyl.
Another specific value for $R_1$ is the formula,

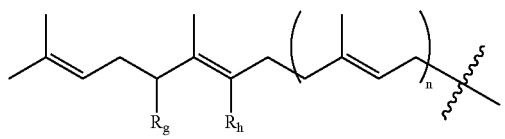

wherein:
n is 0, 1, or 2; and
$R_g$ and $R_h$ together with the atoms to which they are attached form an aryl ring that is optionally substituted with one or more (e.g. 1, 2, 3, or 4) ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or ($C_1$-$C_6$)alkyl.
Another specific value for $R_1$ is of the formula,

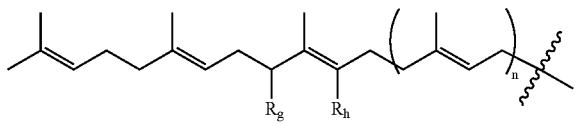

wherein:
n is 0 or 1; and
$R_g$ and $R_h$ together with the atoms to which they are attached form an aryl ring that is optionally substituted with one or more (e.g. 1, 2, 3, or 4) ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or ($C_1$-$C_6$)alkyl.
Another specific value for $R_1$ is the formula,

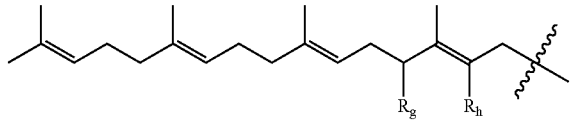

wherein:
$R_g$ and $R_h$ together with the atoms to which they are attached form an aryl ring that is optionally substituted with one or more (e.g. 1, 2, 3, or 4) ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or ($C_1$-$C_6$)alkyl.
Another specific value for $R_1$ is a saturated or unsaturated ($C_5$-$C_{20}$)alkyl chain terminally substituted with $OR_a$ or $NR_bR_c$; wherein $R_a$ is aryl; and each $R_b$ and $R_c$ is independently H, ($C_1$-$C_6$)alkyl, or aryl; wherein any aryl is optionally substituted with one or more carboxy or $S(O)_2NR_dR_e$, wherein each $R_d$ and $R_e$ is independently H or ($C_1$-$C_6$)alkyl.
Another specific value for $R_1$ is the formula,

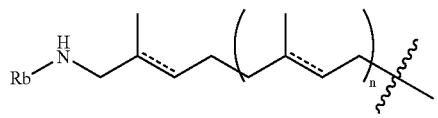

wherein:
n is 0, 1, 2, or 3;
each bond designated by - - - is independently either present or is absent; and
$R_b$ is phenyl or naphthyl and is optionally substituted with one or more carboxy or $S(O)_2NR_dR_e$, wherein each $R_d$ and $R_e$ is independently H or ($C_1$-$C_6$) alkyl.
A specific value for $R_2$ is a saturated or unsaturated ($C_5$-$C_{20}$)alkyl chain.
Another specific value for $R_2$ is an unsaturated ($C_5$-$C_{20}$) alkyl chain.
Another specific value for $R_2$ is a saturated or unsaturated ($C_5$-$C_{20}$)alkyl chain that comprises one or more aryl rings in the chain.
Another specific value for $R_2$ is a saturated or unsaturated ($C_5$-$C_{20}$)alkyl chain that is substituted with one or more halo, trifluoromethyl, $OR_a$ or $NR_bR_c$.
Another specific value for $R_2$ is the formula,

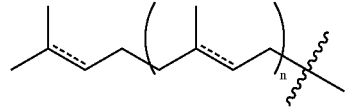

wherein:
n is 0, 1, 2, or 3; and each bond designated by - - - is independently either present or is absent.
Another specific value for $R_2$ is the formula,

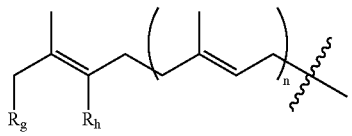

wherein:
n is 0, 1, 2, or 3; and
$R_g$ and $R_h$ together with the atoms to which they are attached form an aryl ring that is optionally substituted with one or more (e.g. 1, 2, 3, or 4) ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

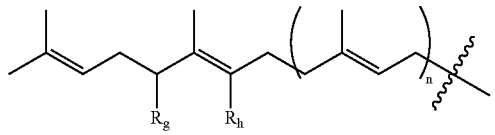

wherein:

n is 0, 1, or 2; and $R_g$ and $R_h$ together with the atoms to which they are attached form an aryl ring that is optionally substituted with one or more (e.g. 1, 2, 3, or 4) $(C_1-C_6)$ alkyl, $(C_1-C_6)$alkoxy, $(C_1-C_6)$alkanoyl, $(C_1-C_6)$alkanoyloxy, $(C_1-C_6)$ alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

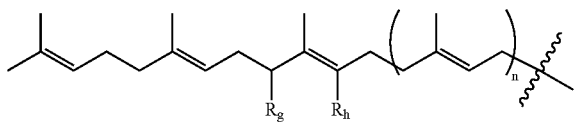

wherein:

n is 0 or 1; and $R_g$ and $R_h$ together with the atoms to which they are attached form an aryl ring that is optionally substituted with one or more (e.g. 1, 2, 3, or 4) $(C_1-C_6)$ alkyl, $(C_1-C_6)$alkoxy, $(C_1-C_6)$alkanoyl, $(C_1-C_6)$alkanoyloxy, $(C_1-C_6)$ alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

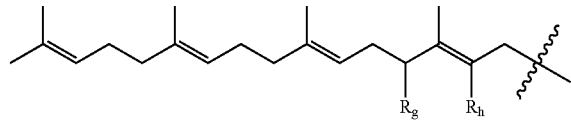

wherein:

$R_g$ and $R_h$ together with the atoms to which they are attached form an aryl ring that is optionally substituted with one or more (e.g. 1, 2, 3, or 4) $(C_1-C_6)$ alkyl, $(C_1-C_6)$alkoxy, $(C_1-C_6)$alkanoyl, $(C_1-C_6)$alkanoyloxy, $(C_1-C_6)$ alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is a saturated or unsaturated $(C_5-C_{20})$alkyl chain terminally substituted with $OR_a$ or $NR_bR_c$; wherein $R_a$ is aryl; and each $R_b$ and $R_c$ is independently H, $(C_1-C_6)$alkyl, or aryl; wherein any aryl is optionally substituted with one or more carboxy or $S(O)_2NR_dR_e$, wherein each $R_d$ and $R_e$ is independently H or $(C_1-C_6)$alkyl.

Another specific value for $R_2$ is of the formula,

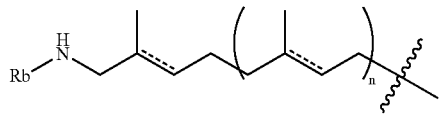

wherein:

n is 0, 1, 2, or 3;

each bond designated by - - - is independently either present or is absent; and $R_b$ is phenyl or naphthyl and is optionally substituted with one or more carboxy or $S(O)_2NR_dR_e$, wherein each $R_d$ and $R_e$ is independently H or $(C_1-C_6)$ alkyl.

A specific value for each of $R_3$, $R_4$, $R_5$, and $R_6$ is OH.

Another specific value for each $R_3$, $R_4$, $R_5$, and $R_6$ is $(C_1-C_6)$alkoxy;

A specific compound of the invention is a prodrug of a compound wherein each $R_3$, $R_4$, $R_5$, and $R_6$ is OH.

Another specific compound of the invention is a prodrug wherein one or more of $R_3$, $R_4$, $R_5$, and $R_6$ is a group that is cleaved in vivo to provide a corresponding compound wherein said one or more of $R_3$, $R_4$, $R_5$, and $R_6$ is OH.

Another specific value for $R_3$, $R_4$, $R_5$, and/or $R_6$ is a pivaloyloxymethyloxy, s-acyl-2-thioethyloxy, or an amino acid.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain embodiments of the present invention provide compounds that act as GGPP synthase inhibitors. While not intended to be a limitation of the present invention, the ability of compounds of the invention to inhibit GGPP synthase will enable the art worker to use these compounds to affect certain processes that are influenced by GGPP synthase. For example, certain embodiments of the present invention provide methods for treating cancer, modulating (e.g., increasing or decreasing) testicular function, modulating (e.g., increasing or decreasing) fertility, treating insulin resistance, treating obesity, modulating (e.g., increasing or decreasing) weight gain, modulating (e.g., increasing or decreasing) osteoclast function, treating a parasitic infection, producing an antiparasitic effect, and for treating cardiac arrhythmia. Certain embodiments of the present invention also provide the use of a compound of the invention to prepare a medicament useful for treating cancer, modulating (e.g., increasing or decreasing) testicular function, modulating (e.g., increasing or decreasing) fertility, treating insulin resistance, treating obesity, modulating (e.g., increasing or decreasing) weight gain, modulating (e.g., increasing or decreasing) osteoclast function, treating a parasitic infection, and for treating cardiac arrhythmia in an animal. Compounds of the invention may also induce different cardiac rhythms, and the compounds thus might also be used to induce the different cardiac rhythms, e.g., reversible asystole, e.g., during a cardiac bypass procedure and to prepare useful medicaments useful for the same. The ability of a compound of the invention to cause these effects can be evaluated by the art worker using assays known in the art.

The invention also provides a detectable compound that is a compound of formula I that includes or that is linked to one or more detectable groups. Detectable groups include, but are not limited to, fluorescent groups and radionuclides. For example, a detectable compound that includes a fluorescent group is exemplified in Example 7. Such compounds are useful, e.g., as probes, e.g., for identifying tissues that include geranylgeranyl pyrophosphate synthase or for illucidating geranylgeranyl pyrophosphate synthase function. The invention also provides tissue including a compound of the invention bound to geranylgeranyl pyrophosphate synthase.

In one embodiment, the detectable group is not a six-membered aromatic ring containing one or more nitrogen atoms.

Detectable compounds of the invention, e.g., radiolabeled compounds of formula I, are useful as imaging agents for imaging cells and tissues that include geranylgeranyl pyrophosphate synthase. Accordingly, the invention also provides compounds of formula I that include or that are linked to one or more detectable radionuclides (e.g., one or more metallic radionuclide and/or one or more non-metallic radionuclides). For example, a detectable radionuclide can be incorporated into a compound by replacing an atom of the compound of formula I with a radionuclide (e.g., non-metallic radionuclide). Alternatively, a radiolabeled compound of the invention can be prepared by linking a compound of formula I to a chelating group that includes a detectable radionuclide (e.g., metallic radionuclide). Methods for making such detectable compounds are known to the art worker. Such compounds can be useful to image tissues with geranylgeranyl pyrophosphate synthase activity in vivo or in vitro.

As used herein, a "chelating group" is a group that can include a detectable group, e.g., a radionuclide (e.g., a metallic radioisotope). Any suitable chelating group can be employed. Suitable chelating groups are disclosed, e.g., in Poster Sessions, Proceedings of the 46th Annual Meeting, J. Nuc. Med., p. 316, No. 1386; Scientific Papers, Proceedings of the 46th Annual Meeting, J. Nuc. Med., p. 123, No. 499; Scientific Papers, Proceedings of the 46th Annual Meeting, J. Nuc. Med., p. 102, No. 413; Scientific Papers, Proceedings of the 46th Annual Meeting, J. Nuc. Med., p. 102, No. 414; Scientific Papers, Proceedings of the 46th Annual Meeting, J. Nuc. Med., p. 103, No. 415; Poster Sessions, Proceedings of the 46th Annual Meeting, J. Nuc. Med., p. 318, No. 1396; Poster Sessions, Proceedings of the 46th Annual Meeting, J. Nuc. Med., p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); C. J. Anderson et al., J. Nucl. Med. 36, 850 (1995); U.S. Pat. No. 5,739,313; and U.S. Pat. No. 6,004,533.

As used herein, a "detectable radionuclide" is any suitable radionuclide (i.e., a radioisotope) useful in an imaging procedure, e.g., a diagnostic procedure, in vivo or in vitro. Suitable detectable radionuclides include metallic radionuclides (i.e., metallic radioisotopes) and non-metallic radionuclides (i.e., non-metallic radioisotopes).

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

In some embodiments of the invention, the chelating group can include more than one metallic radioisotope. In some embodiments, the detectable chelating group can include 2 to about 10, 2 to about 8, 2 to about 6, or 2 to about 4 metallic radioisotopes.

The non-metallic radionuclide can be a non-metallic paramagnetic atom (e.g., Fluorine-19); or a non-metallic positron emitting radionuclide (e.g., Carbon-11, Fluorine-18, Iodine-123, or Bromine-76). In some embodiments of the invention, the non-metallic radionuclide is phosphorous-32.

In some embodiments of the invention, the compounds of the present invention can include more than one non-metallic radioisotope. In some embodiments, the compounds of the present invention can include 2 to about 10, 2 to about 8, 2 to about 6, or 2 to about 4 non-metallic radioisotopes.

The ability of a compound of the invention to act as an inhibitor of geranylgeranyl pyrophosphate synthase may be determined using pharmacological models which are well known to the art, for example see Holstein, S. A., et al., *Biochemistry* 2003, 42, 4384-4391; and Ericsson et al, *J. Biological Chemistry*, 1993, 268, 832-838. The ability of a compound to inhibit FPP synthase, FPTase, and GGPTase can also be determined using pharmacological models which are well known to the art. The selectivity of a compound as an inhibitor of geranylgeranyl pyrophosphate synthase can be evaluated by comparing it's inhibitory activity against this enzyme with it's activity against another enzyme. In one embodiment of the invention, the compound of the invention is at least 2-fold selective for inhibiting geranylgeranyl pyrophosphate synthase compared to farnesylpyrophosphate. In another embodiment the compound is at least 10-fold selective for inhibiting geranylgeranyl pyrophosphate synthase compared to farnesylpyrophosphate. In another embodiment the compound is at least about 100-fold selective for inhibiting geranylgeranyl pyrophosphate synthase compared to farnesylpyrophosphate. In another embodiment of the invention, the compound of the invention is at least 2-fold selective for inhibiting geranylgeranyl pyrophosphate synthase compared to FPTase or GGPTase. In another embodiment the compound is at least 10-fold selective for inhibiting geranylgeranyl pyrophosphate synthase compared to FPTase or GGPTase. In another embodiment the compound is at least about 100-fold selective for inhibiting geranylgeranyl pyrophosphate synthase compared to FPTase or GGPTase.

Compounds (12 and 13) have been tested against mammalian GGPP synthase, FPP synthase, FPTase, and GGPTase. The enzymatic data indicates that these compounds selectively inhibit GGPP synthase. At the 1 to 10 nanomolar range that inhibits GGPP synthase by 50% there is no inhibition of FPP synthase, FPTase or GGPTase. These other enzymes are not inhibited at concentrations as high as 50 micromolar.

The compounds have also been tested for activities against human leukemia cells (K562), breast cancer cells (MCF-7), myeloma cells (RPMI-8226), murine fibroblasts (NIH 3T3), and murine bone marrow cells (32D). In all of these cell lines the compounds have similar activities to decrease GGPP, but not FPP levels. The concentrations of the compounds that product the effects in intact cells are in the micromolar range. Depletion of GGPP markedly increases levels of unmodified Rap1a, an anti-RAS oncogene that interferes with RAS-mediated signal transduction. There is also evidence that these compounds decrease phosphorylation of stat in erythropoietin stimulated 32D cells.

General Experimental Procedures

Representative compounds of the invention can generally be prepared as illustrated in the following Schemes 1-6 though variations of literature procedures for alkylation of methylene bisphosphonate esters (for example, see Ebetino, F. H., et al., *Heterocycles*, 1990, 30, 855-862). As shown in Scheme 1, when one equivalent of geranyl bromide (1) was allowed to react with commercial tetraethyl methylenebisphosphonate (2) the monoalkyl geranylbisphosphonate (3) could be obtained in good yield (see Holstein, S. A., et al., *Bioorganic & Medicinal Chemistry*, 1998, 6, 687-694). When tetramethyl methylenebisphosphonate (4) was used under similar reaction conditions, the corresponding tetramethyl ester (5) was obtained in lower yield. The lower yield was due, at least in part, to formation of a by-product where a methyl ester had been replaced with a geranyl group.

Scheme 1.
Synthesis of isoprenoid monoalkyl bisphonates from geranyl bromide.

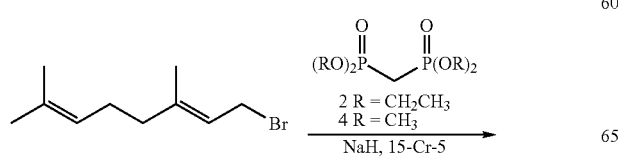

-continued

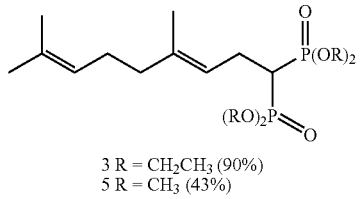

3 R = CH$_2$CH$_3$ (90%)
5 R = CH$_3$ (43%)

To favor formation of symmetrical dialkyl bisphosphonates, the alkylating agent was used in excess as shown in Scheme 2 with geranyl bromide (2).

Scheme 2.
Synthesis of isoprenoid dialkyl bisphosphonates from geranyl bromide.

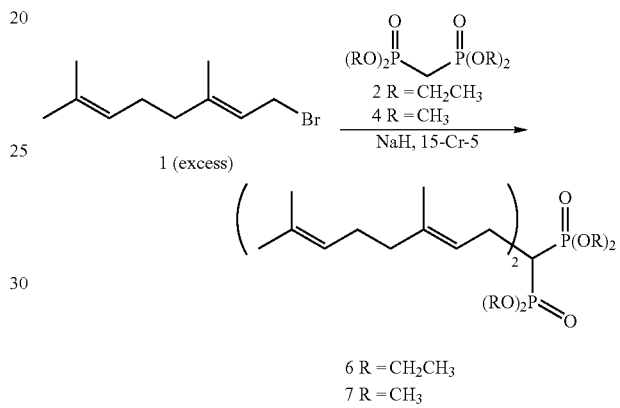

6 R = CH$_2$CH$_3$
7 R = CH$_3$

To prepare unsymmetrical dialkyl compounds, a monoalkyl bisphosphonate was first prepared, and then treated with base and a second alkylating agent. So for example (Scheme 3), farnesyl bromide (8) was allowed to react with bisphosphonate (2) to obtain compound (9), and after purification compound (9) was treated with base and isoprenyl bromide (10) to obtain the unsymmetrical dialkylbisphosphonate (11).

Scheme 3.
Synthesis of an unsymmetrical dialkyl biphosphonates from farnesyl bromide.

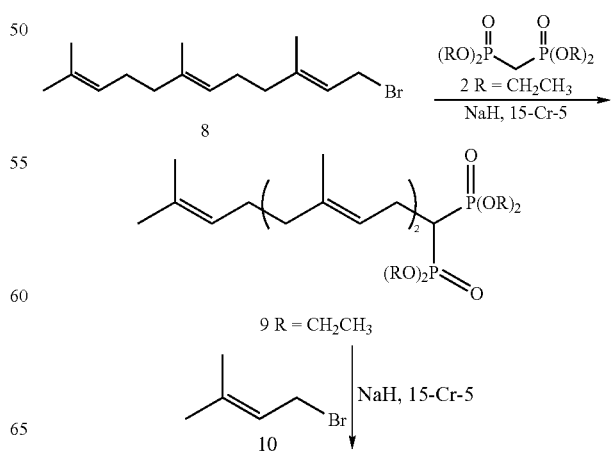

9 R = CH$_2$CH$_3$

-continued

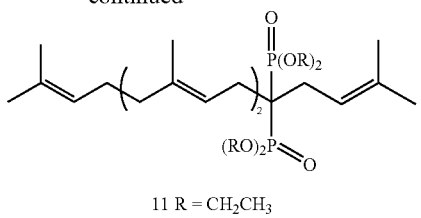

11 R = CH₂CH₃

To obtain salts for bioassay, the mono, symmetrical dialkyl, or unsymmetrical dialkyl bisphosphonates were treated with trimethylsilyl bromide and base, through minor variations of the procedure of McKenna (McKenna, C. E., et al., *Tetrahedron Lett.*, 1977, 18, 155-158). For example, as shown in Scheme 4, treatment of compound (6) under these conditions gave the tetrasodium salt (12).

Scheme 4.
Synthesis of a dialkyl bisphosphonate tetrasodium salt.

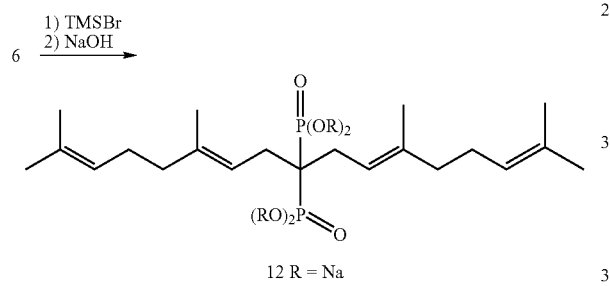

12 R = Na

To obtain bisphosphonate prodrug derivatives (e.g., esters) that would be expected to be cleaved after cellular uptake, tetramethyl esters of the bisphosphonates were treated with sodium iodide and pivaloyloxymethyl chloride (POM-Cl), through a minor variations of the procedure of Vepsäläinen (Vepsäläinen, J. J. *Tetrahedron Lett.*, 1999, 40, 8491-8493). For example, as shown in Scheme 5, reaction of the tetramethyl ester (7) with POM-Cl under these conditions gave the tetra POM ester (13).

Scheme 5.
Synthesis of a dialkyl bisphosphonate as the tetraPOM ester.

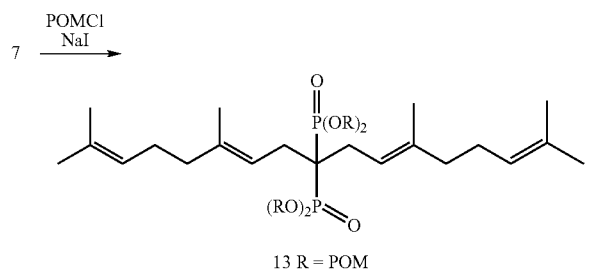

13 R = POM

Derivatives of the unsymmetrical dialkyl bisphosphonates could be obtained through parallel reactions. Thus, for example treatment of the tetraethyl ester (11) with TMSBr and base gave the sodium salt (14) (Scheme 6).

Scheme 6.
Synthesis of an unsymmetrical dialkyl bisphosphonate tetrasodium salt.

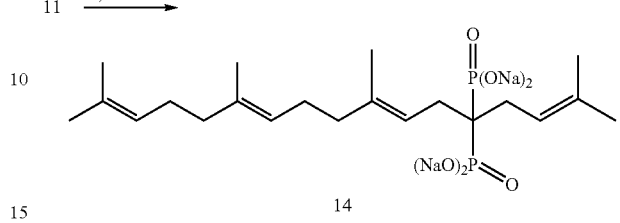

14

The invention will now be illustrated by the following non-limiting

EXAMPLES

Example 1

Synthesis of tetramethyl (E)-1,1-bis(4,8-dimethyl-nona-3,7-dienyl)-1,1-bisphosphonate (7)

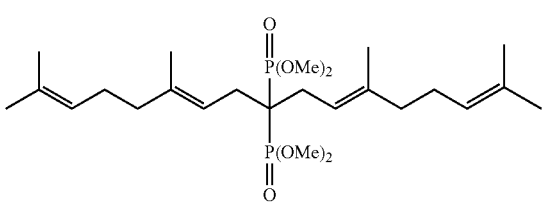

To a stirred suspension of NaH (0.37 g, 9.35 mmol, washed with hexanes (3×20 mL) and dried in vacuo) in THF (10 mL), 15-crown-5 (0.17 mL, 0.84 mmol) was added via syringe at 0° C. over 15 minutes. Tetramethylmethylene bisphosphonate (2.04 mL, 8.78 mmol) was added as a neat liquid to the NaH suspension over 10 minutes, and the reaction mixture was allowed to stir for 30 minutes. Geranyl bromide (1.8 mL, 9.45 mmol) was added dropwise as a neat liquid and the resulting solution was stirred for 2 h, and then filtered through celite and concentrated in vacuo. The resulting yellow oil was purified by flash chromatography (gradient, 0-5% methanol in Et₂O) affording compound (7). 0.65 g, 15%; $^1$H NMR δ 5.37 (t, J=6.7 Hz, 2H), 5.11 (t, J=6.5 Hz, 2H), 3.80 (d, J=10.8 Hz, 12H), 2.62 (td, J=15.9, 7.0 Hz, 4H), 2.11-2.02 (m, 8H), 1.67 (s, 6H), 1.62 (s, 6H), 1.60 (s, 6H); $^{13}$C NMR δ 127.4 (2C), 131.1 (2C), 124.2 (2C), 118.8 (t, J=7.4 Hz, 2C), 53.1-53.0 (m, 4C), 46.3 (t, J=131.4 Hz), 39.9 (2C), 28.9 (t, J=4.4 Hz, 2C), 26.5 (2C), 25.5 (2C), 17.5 (2C), 16.1 (2C); $^{31}$P NMR +28.8 ppm. Anal. Calcd for $C_{25}H_{46}O_6P_2 \cdot 0.5\ H_2O$: C, 58.47; H, 9.22. Found: C, 58.52; H, 9.18.

Compound (5) Tetramethyl (E)-4,8-dimethyl-nona-3,7-dienyl-1,1-bisphosphonate was also isolated from the reaction mixture. (1.43 g, 45%): $^1$H NMR δ 5.27 (t, J=6.8 Hz, 1H), 5.09 (t, J=6.7 Hz, 1H), 3.83 (d, J=1.7 Hz, 6H), 3.79 (d, J=1.7 Hz, 6H), 2.64 (tt, J=17.2, 7.0 Hz, 2H), 2.38 (tt, J=24.0, 5.7 Hz, 1H), 2.16-1.16 (m, 4H), 1.68 (s, 3H), 1.65 (s, 3H), 1.60 (s, 3H); $^{13}$C NMR δ 137.1, 131.2, 123.9, 121.2 (t, J=7.2 Hz), 53.1-52.9 (m, 4C), 39.5, 36.5 (t, J=133.1 Hz), 26.4, 25.5, 23.8 (t, J=5.0 Hz), 17.5, 15.9; $^{31}$P NMR +25.7 ppm. Anal. Calcd for $C_{15}H_{30}O_6P_2$: C, 48.91; H, 8.21. Found: C, 48.74; H, 8.31.

Example 2

Synthesis of tetraethyl 4,8-dimethyl-3,7-nonadienyl-1,1-bisphosphonate (6)

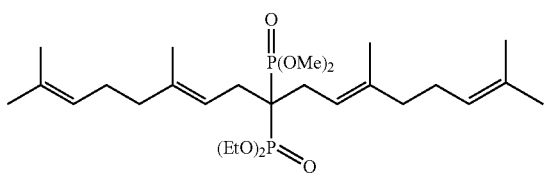

6

To a stirred suspension of NaH (349 mg, 10.2 mmol, washed with hexanes (3×20 mL) and dried in vacuo) in THF (10 mL), 15-crown-5 (0.17 mL, 0.84 mmol) was added via syringe at 0° C. over 15 minutes. Tetraethyl methylenebisphosphonate (1.01 mL, 4.0 mmol) was added as a neat liquid to the NaH suspension over 10 minutes and the reaction mixture was allowed to stir for 30 minutes. Geranyl bromide (2.34 mL, 10.0 mmol) was added as a neat liquid at 0° C., the resulting solution was stirred for 1 h, and then quenched by addition of $NH_4Cl$ (20 mL) and water (10 mL). The reaction mixture was extracted with ether, dried ($MgSO_4$), filtered, and the filtrate was concentrated in vacuo. The resulting yellow oil was purified by flash chromatography (gradient, 5-10% methanol in $Et_2O$) resulting in a pale-yellow oil (1.89 g, 85%): $^1$H NMR ($CDCl_3$) δ 5.43 (t, J=6.9 Hz, 2H), 5.11 (tt, J=6.8, 1.4 Hz, 2H), 4.17 (p, J=7.7 Hz, 8H), 2.63 (dt, J=16.0, 7.1 Hz, 4H), 2.09-2.00 (m, 8H), 1.67 (s, 6H), 1.62 (s, 6H), 1.59 (s, 6H), 1.32 (t, J=7.1 Hz, 12H); $^{13}$C NMR δ 137.1 (2C), 131.4 (2C), 124.5 (2C), 119.5 (t, J=7.3 Hz, 2C), 62.6-62.4 (m, 4C), 46.1 (t, J=131.1 Hz), 40.3 (2C), 29.3 (t, J=4.4 Hz, 2C), 26.8 (2C), 25.8 (2C), 17.8 (2C), 16.7-16.6 (m, 4C), 16.4 (2C); $^{31}$P NMR +26.7 ppm. Anal. Calcd for $C_{29}H_{54}P_2O_6 \cdot 0.5 H_2O$: C, 61.14; H, 9.73. Found: C, 61.23; H, 9.70.

Example 3

Synthesis of tetraethyl (2E,6E)-1-(3-methyl-but-2-enyl)-3,7,11-trimethyl-dodeca-2,6,10-trienyl-1,1-bisphosphonate (11)

11

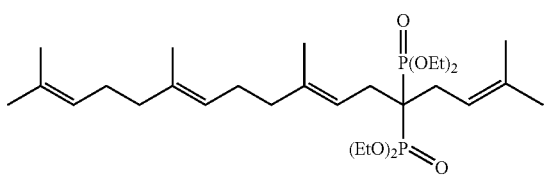

To a stirred solution of farnesyl bisphosphonate 9 (507 mg, 0.95 mmol, see Holstein, S. A., et al., *Bioorganic & Medicinal Chemistry*, 1998, 6, 687-694) was added 15-Cr-5 (0.02 mL, 0.1 mmol) and NaH (66 mg, 1.65 mmol) as a neat liquid and solid, respectively. After 1 hour, prenyl bromide was added as a neat liquid and the reaction mixture was allowed to stir for 20 minutes. The reaction mixture was quenched by addition of $NH_4Cl$ (sat) and extracted into ether. The combined organic extracts were dried ($MgSO_4$), and concentrated in vacuo to produce a yellow oil. The oil was purified by flash chromatography (1% methanol in ether) to afford a yellow oil 11 (429 mg, 81 %): $^1$H NMR δ 5.46-5.37 (m, 2H), 5.15-5.07 (m, 2H), 4.17 (p, J=7.4 Hz, 8H), 2.70-2.55 (m, 4H), 2.08-1.94 (m, 8H), 1.71 (s, 3H), 1.68 (s, 3H), 1.62 (s, 6H), 1.60 (s, 6H), 1.32 (t, J=7.1 Hz, 12H); $^{13}$C NMR δ 137.1, 135.0, 133.2, 131.2, 124.4, 124.3, 119.7 (t, J=7.2 Hz), 119.3 (t, J=7.3 Hz), 62.5-62.2 (m, 4C), 46.0 (t, J=131.3 Hz), 40.2, 39.8, 30.4, 29.3 (t, J=4.5 Hz), 29.2 (t, J=4.5 Hz), 26.8, 26.7, 26.1, 25.7, 17.9, 17.7, 16.5 (t, J=3.1 Hz, 4C), 16.3, 16.0; $^{31}$P NMR +26.4 ppm. Anal. Calcd for $C_{29}H_{54}O_6P_2$: C, 62.12; H, 9.71. Found: C, 62.33; H, 9.81.

Example 4

Synthesis of 1-(3,7-dimethyl-octa-2,6-dienyl)-4,8-dimethyl-nona-3,7-dienyl-1,1-bisphosphonic acid, tetrasodium salt (12)

12

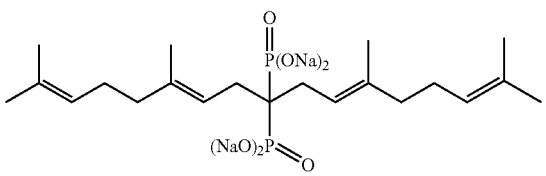

Compound 6 was treated with trimethylsilyl bromide and base (NaOH) to provide compound 12 (160 mg, 79%): $^1$H NMR ($CD_3OD$) δ 5.80 (t, J=6.3 Hz, 2H), 5.13 (t, J=6.0 Hz, 2H), 2.69 (dt, J=14.8, 6.9 Hz, 4H), 2.10-1.99 (m, 8H), 1.67 (s, 6H), 1.61 (brs, 12H); $^{13}$C NMR δ 135.5 (2C), 131.7 (2C), 126.1 (2C), 124.2-124.1 (t, $J_{CP}$=7.8 Hz, 2C), 46.9-43.9 (t, $J_{CP}$=110.9 Hz), 41.6 (2C), 29.7 (t, J=7.8 Hz, 2C), 28.3 (2C), 26.0 (2C), 17.9 (2C), 16.5 (2C); $^{31}$P NMR +24.3 ppm; HRMS (ES) m/z: calcd for (M–H)$^-$ $C_{21}H_{37}P_2O_6$, 447.2065; found, 447.2066.

Example 5

Synthesis of tetrapivaloyloxymethyl (E)-1,1-bis(4,8-dimethyl-nona-3,7-dienyl)-1,1-bisphosphonate (13)

13

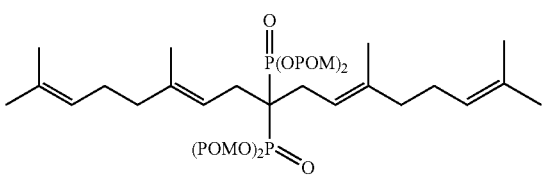

To a stirred suspension of bisphosphonate 7 (306 mg, 0.61 mmol) in acetonitrile (10 mL) was added NaI (376.2 mg, 2.46 mmol) and POMCl (0.45 mL, 3.09 mmol) as a neat solid and liquid, respectively, at room temperature. The reaction mixture was heated at reflux for 18 hours and then quenched by addition of ether (25 mL) and water (10 mL). This mixture was extracted into ether, dried (MgSO$_4$), and concentrated in vacuo. The resulting oil was purified with flash chromatography (40% hexane in ether) to afford a yellow oil 13 (99.0 mg, 18%): $^1$H NMR δ 5.75-5.65 (m, 8H), 5.31 (t, J=7.1 Hz, 2H), 5.08 (t, J=6.6 Hz, 2H), 2.62 (td, J=16.7, 7.2 Hz, 4H), 2.10-1.95 (m, 8H), 1.67 (s, 6H), 1.61 (s, 6H), 1.59 (s, 6H), 1.23 (s, 36H); $^{13}$C NMR δ 176.9 (4C), 139.0 (2C), 131.6 (2C), 124.4 (2C), 117.9 (t, J=7.6 Hz, 2C), 82.4 (t, J=2.8 Hz, 4C), 46.6 (t, J=131.4 Hz), 40.3 (2C), 38.9 (4C), 28.7 (t, J=, 2C), 27.1 (12C), 26.8 (2C), 25.9 (2C), 17.9 (2C), 16.4 (2C); $^{31}$P NMR +25.0 ppm. Anal. Calcd for C$_{45}$H$_{78}$O$_{14}$P$_2$: C, 59.72; H, 8.69. Found: C, 59.72; H, 8.71.

Example 6

Synthesis of (2E,6E)-1-(3-methyl-but-2-enyl)-3,7,11-trimethyl-dodeca-2,6,10-triene-1,1-bisphosphonate (14)

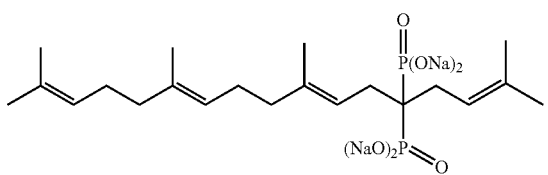

Compound 11 was treated with trimethylsilyl bromide and base (NaOH) to provide compound 14 (156 mg, 81%); $^1$H NMR (CD$_3$OD) δ 5.93-5.80 (m, 2H), 5.15-5.08 (m, 2H), 2.63-2.42 (m, 4H), 2.15-1.91 (m, 8H), 1.70 (s, 3H), 1.68 (s, 3H), 1.61 (s, 12H); $^{13}$C NMR δ 135.3, 134.3, 132.1, 129.8, 126.9-126.6 (m), 126.5, 125.7, 41.9, 41.1 (2C), 32.0-31.7 (m), 28.6, 28.0 (2C), 26.5, 26.0 (2C), 18.5, 17.9, 16.4, 16.2; $^{31}$P NMR +26.9 ppm; HRMS (neg. ion ESI) m/z: calcd for (M−H)$^−$ C$_{21}$H$_{37}$O$_6$P$_2$, 447.2065; found, 447.2052.

Example 7

Synthesis of an Example of a Fluorescent Compound (15)

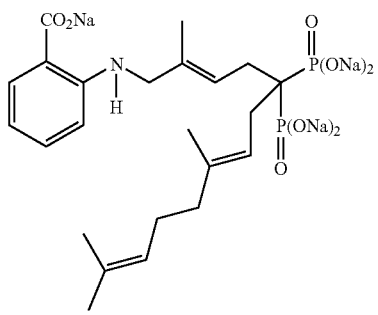

To a solution of the amino bisphosphonate from step d below (86 mg, 0.13 mmol) in anhydrous CH$_2$Cl$_2$ at 0° C. was added 2,4,6-collidine (0.18 mL, 1.3 mmol) and TMSBr (0.17 mL, 1.3 mmol), and the reaction mixture was allowed to warm to room temperature over a period of 18 hours. Toluene was then added to the reaction mixture, and the volatiles were removed in vacuo to afford a white solid. The solid was dissolved in aqueous NaOH (7 mL, 1 N) at rt, stirred for 2 days, and the reaction mixture then was poured into acetone. The biphasic layer was stored at 4° C. for 4 days, and then filtered to afford compound 15 as a white solid: $^{31}$P NMR (D$_2$O) δ 25.3.

The intermediate amino bisphosphonate compound used to prepare compound 15 was prepared as follows.

a. Methyl 2-(N-2-methyl-4-tert-butylsilyloxy-2-butenyl)amino benzoate

To a solution of 2-methyl-4-tert-butylsilyloxy-2-butenal (0.80 g, 3.7 mmol) and methyl anthranilate (0.54 mL, 4.1 mmol) in anhydrous dichloroethane was added molecular sieves (4 Å) and glacial acetic acid (0.26 mL, 4.5 mmol). The resulting mixture was allowed to stir at room temperature for 5 minutes, and then sodium triacetoxy borohydride (1.2 g, 5.2 mmol) was added. After the reaction was stirred for 3.5 hours at room temperature, saturated NaHCO$_3$ was added dropwise at 0° C. The aqueous layer was extracted with ether and the combined organic extract was dried (MgSO$_4$) and then filtered. The filtrate was concentrated and the resulting residue was purified by flash chromatography (99:1 hexanes:EtOAc) to give the methyl 2-(N-2-methyl-4-tert-butylsilyloxy-2-butenyl)amino benzoate (0.88 g, 68%) as a yellow oil: $^1$H NMR (300 MHz, CDCl$_3$) δ 7.92-7.89 (m, 2H), 7.35-7.27 (m, 1H), 6.66-6.56 (m, 2H), 5.62-5.57 (m, 1H), 4.26-4.24 (m, 2H), 3.86 (s, 3H), 3.78 (d, J=4.5 Hz, 2H), 1.70 (s, 3H), 0.90 (s, 9H), 0.06 (s, 6H); $^{13}$C NMR (75 MHz) δ 169.3, 151.4, 134.7, 133.3, 131.7, 126.1, 114.8, 111.9, 110.2, 60.2, 51.6, 50.4, 26.2 (3C), 18.6, 14.9, −4.9 (2C).

b. Methyl 2-(N-2-methyl-4-hydroxy-2-butenyl)amino benzoate

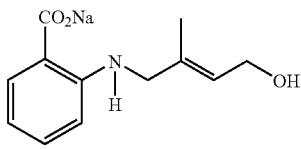

To a solution of methyl 2-(N-2-methyl-4-tert-butylsilyloxy-2-butenyl)amino benzoate. (0.84 g, 2.4 mmol) in THF at 0° C. was added TBAF (4.8 mL, 1 M in THF) and the reaction mixture was allowed to warm to room temperature over a period of 1.75 hours. The reaction was quenched by addition of saturated NH$_4$Cl and extracted with ether. The combined organic extract was dried (MgSO$_4$) and then filtered. The filtrate was concentrated and the resulting residue was purified by flash chromatography (80:20 hexanes:EtOAc) to give methyl 2-(N-2-methyl-4-hydroxy-2-butenyl)amino benzoate (0.51 g, 90%) as a yellow oil:. $^1$H NMR (300 MHz, CDCl$_3$) δ 7.91-7.89 (m, 2H), 7.34-7.26 (m, 1H), 6.62-6.59 (m, 2H), 5.68-5.63 (m, 1H), 4.20 (d, J=6.6 Hz, 2H), 3.86 (s, 3H), 3.79 (d, J=5.7 Hz, 2H), 1.73 (s, 3H), 1.41 (br s, 1H); $^{13}$C NMR (75 MHz) δ 169.3, 151.3, 135.6, 134.7, 131.8, 124.5, 114.9, 111.7, 110.2, 59.3, 51.7, 50.1, 14.9.

c. Tetraethyl 4,8-dimethyl-3,7-nonadienyl-1,1-bisphosphonate

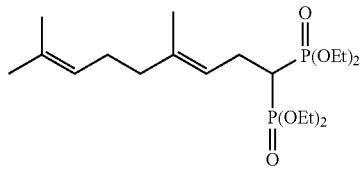

To a suspension of NaH (0.17 g, 4.2 mmol) in anhydrous THF at 0° C. was added 15-crown-5 (15C5) (0.08 mL, 0.4 mmol) followed by tetraethylmethylene-diphosphonate (1.2 g, 4.2 mmol). After the reaction mixture was stirred for 30 minutes, geranyl bromide (1.0 g, 4.6 mmol) in THF was added via cannula. The reaction mixture was allowed to warm to room temperature over 5 hours, and then water was added. The aqueous layer was extracted with ether and the combined organic layer was dried (MgSO$_4$) and filtered. The filtrate was concentrated and the resulting oil was purified by flash chromatography (4% MeOH in ether) to give the desired bisphosphonate (0.91 g, 23%) as a yellow oil. Both $^1$H and $^{31}$P NMR spectra agree with literature data. This compound can also be prepared as illustrated hereinabove for compound 3.

d. Compound 15

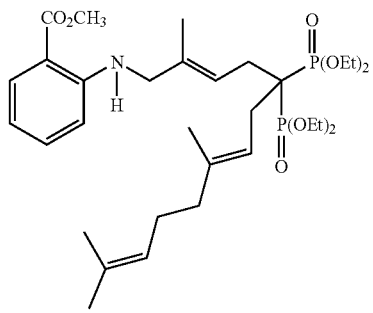

N-Chlorosuccinimide (0.65 g, 4.9 mmol) was dissolved in anhydrous CH$_2$Cl$_2$ and stirred under argon. The stirred mixture was put in an acetonitrile/dry ice bath at −40° C. Dimethyl sulfide (0.39 mL, 5.3 mmol) was added dropwise to the stirred mixture, and then it was allowed to warm to 0° C. in an ice bath and kept at this temperature for 15 minutes. The reaction mixture was cooled to −40° C., and a solution of methyl 2-(N-2-methyl-4-hydroxy-2-butenyl)amino benzoate (1.0 g, 4.4 mmol) in anhydrous CH$_2$Cl$_2$ was slowly transferred to the cooled mixture via cannula. The reaction mixture was allowed to warm to room temperature over a period of 3 hours, and then transferred to a separatory funnel containing ice-cold brine. The aqueous layer was extracted with pentane and then ether. The combined organic layer was dried (Na$_2$SO$_4$) and filtered. Removal of the solvent in vacuo afforded the corresponding allylic chloride as a yellow oil that was dried in vacuo and then used without further purification. To a suspension of NaH (85 mg, 2.1 mmol) in anhydrous THF at 0° C. was added 15C5 (2 drops) followed by the bisphosphonate from step c above (0.91 g, 2.1 mmol). After the reaction mixture was stirred for 1 hour, the allylic chloride (0.27 g, 1.1 mmol) in THF was added via cannula. The reaction was allowed to warm to room temperature over 2 hours and then quenched by addition of water. The aqueous layer was extracted with ether and the combined organic layer was dried (MgSO$_4$) and filtered. The filtrate was concentrated and the resulting residue was purified by flash chromatography (4% MeOH in ether) to give bisphosphonate amine (86 mg, 13%) as a yellow oil: $^{13}$C NMR (75 MHz) δ 168.8, 151.6, 137.4, 134.5, 133.7, 131.6, 131.5, 124.5, 121.6 (t, J$_{CP}$=7.3 Hz), 119.2 (t, J$_{CP}$=7.3 Hz), 114.5, 111.9, 110.2, 62.6 (t, J$_{CP}$=3.4 Hz, 4C), 60.3, 51.0, 45.9 (t, J$_{CP}$=131.6 Hz), 40.3, 36.8 (d, J$_{CP}$=3.96 Hz, 2C), 29.2, 26.8, 25.9, 17.8, 16.6 (t, J$_{CP}$=3.1 Hz, 2C), 16.4, 14.8, 14.5; $^{31}$P NMR 627.1.

Example 8

The following illustrate representative pharmaceutical dosage forms, containing a compound of formula I ('Compound X'), for therapeutic and/or prophylactic use in humans.

| (i) Tablet 1 | mg/tablet |
| --- | --- |
| >Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| >Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| >Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
| --- | --- |
| >Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
| --- | --- |
| >Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
| --- | --- |
| >Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An unsymmetrical bisphosphonate compound of formula I:

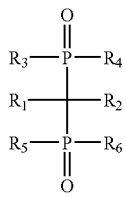

wherein:
$R_1$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;

$R_2$ is a saturated or unsaturated $(C_5-C_{20})$alkyl chain that optionally comprises one or more aryl rings in the chain and that is optionally substituted with one or more halo, trifluoromethyl, $-OR_a$, $P(=O)(OR_a)_2$, or $-NR_bR_c$;

each $R_3$, $R_4$, $R_5$ and $R_6$ is independently OH or $(C_1-C_6)$alkoxy;

each $R_a$ is independently H, $(C_1-C_6)$alkyl, or aryl; and each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;

wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl; and wherein $R_1$ is not equal to $R_2$;

or a pharmaceutically acceptable salt or prodrug thereof.

2. The compound of claim 1 wherein $R_1$ is a saturated or unsaturated $(C_5-C_{20})$alkyl chain.

3. The compound of claim 1 wherein $R_1$ is an unsaturated $(C_5-C_{20})$alkyl chain.

4. A compound of formula I:

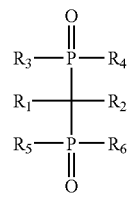

wherein:
$R_1$ is a saturated or unsaturated $(C_5-C_{20})$alkyl chain tat comprises one or more aryl rings in the chain;

$R_2$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_b R_c$;

each $R_3$, $R_4$, $R_5$, and $R_6$ is independently OH or $(C_1-C_6)$alkoxy;

each $R_a$ is independently H, $(C_1-C_6)$alkyl, or aryl; and each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;

wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_c$, or $S(O)_2NR_dR_e$, wherein each $R_d$ and $R_e$ is independently H or $(C_1-C_6)$alkyl;

or a pharmaceutically acceptable salt or prodrug thereof.

5. A compound of formula I:

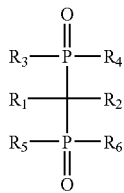

wherein:
- $R_1$ is a saturated or unsaturated $(C_5-C_{20})$alkyl chain that is substituted with one or more halo, trifluoromethyl, $OR_a$ or $NR_bR_c$;
- $R_2$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;
- each $R_3$, $R_4$, $R_5$, and $R_6$ is independently OH or $(C_1-C_6)$alkoxy;
- each $R_a$ is independently H, $(C_1-C_6)$alkyl, or aryl; and
- each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;
- wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl;

or a pharmaceutically acceptable salt or prodrug thereof.

6. A compound of formula I:

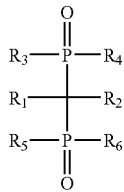

wherein:
$R_1$ is of the formula,

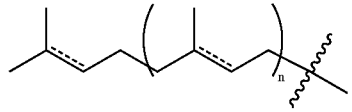

wherein n is 0, 1, or 3; and each bond designated by - - - is independently either present or is absent;
- $R_2$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;
- each $R_3$, $R_4$, $R_5$, and $R_6$ is independently OH or $(C_1-C_6)$alkoxy;
- each $R_a$ is independently H, $(C_1-C_6)$alkyl, or aryl; and
- each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;
- wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl;

or a pharmaceutically acceptable salt or prodrug thereof.

7. The compound of claim 6 wherein each bond designated by - - - is present.

8. The compound of claim 6 wherein n is 0.

9. The compound of claim 6 wherein n is 1.

10. The compound of claim 6 wherein n is 3.

11. The compound of claim 4 wherein $R_1$ is of the formula,

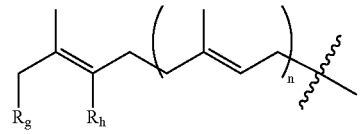

wherein:
- n is 0, 1, 2, or 3; and
- $R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

12. The compound of claim 4 wherein $R_1$ is of the formula,

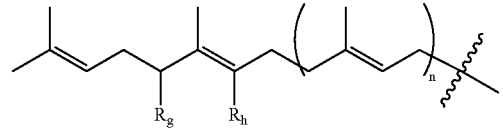

wherein:
- n is 0, 1, or 2; and
- $R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

13. The compound of claim 4 wherein $R_1$ is of the formula,

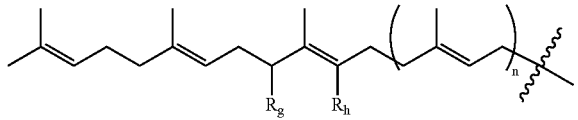

wherein:
  a is 0 or 1; and
  $R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

14. The compound of claim 4 wherein $R_1$ is of the formula,

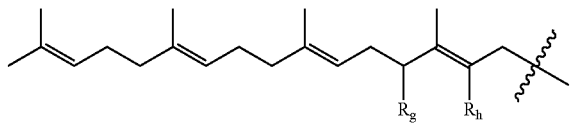

wherein:
  $R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

15. A compound of formula I:

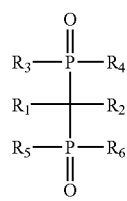

I wherein:
  $R_1$ is a saturated or unsaturated $(C_5-C_{20})$alkyl chain terminally substituted with $OR_a$ or $NR_bR_c$; wherein $R_a$ is aryl; and each $R_b$, and $R_c$ is independently H, $(C_1-C_6)$alkyl, or aryl; wherein any aryl is optionally substituted with one or more carboxy or $S(O)_2NR_dR_e$, wherein each $R_d$ and $R_e$ is independently H or $(C_1-C_6)$alkyl;
  $R_2$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;
  each $R_3$, $R_4$, $R_5$, and $R_6$ is independently OH or $(C_1-C_6)$alkoxy;
  each $R_a$ is independently H, $(C_1-C_6)$alkyl, or aryl; and
  each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;
  wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1C_6)$alkyl;
  or a pharmaceutically acceptable salt or prodrug thereof.

16. The compound of claim 15 wherein $R_1$ is of the formula,

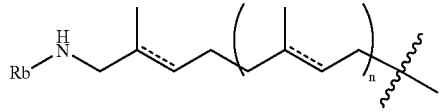

wherein:
  n is 0, 1, 2, or 3;
  each bond designated by - - - is independently either present or is absent; and
  $R_b$ is phenyl or naphthyl and is optionally substituted with one or more carboxy or $S(O)_2NR_dR_e$ wherein each $R_d$ and $R_e$ is independently H or $(C_1-C_6)$alkyl.

17. The compound of claim 16 wherein each bond designated by - - - is present.

18. The compound of claim 11 wherein $R_2$ is a saturated or unsaturated $(C_5-C_{20})$alkyl chain.

19. The compound of claim 11 wherein $R_2$ is an unsaturated $(C_5-C_{20})$alkyl chain.

20. The compound of claim 11 wherein $R_2$ is a saturated or unsaturated $(C_5-C_{20})$alkyl chain that comprises one or more aryl rings in the chain.

21. The compound of claim 11 wherein $R_2$ is a saturated or unsaturated $(C_5-C_{20})$alkyl chain that is substituted with one or more halo, trifluoromethyl, $OR_a$ or $NR_bR_c$.

22. The compound of claim 11 wherein $R_2$ is of the formula,

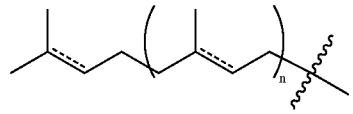

wherein n is 0, 1, 2, or 3; and each bond designated by - - - is independently either present or is absent.

23. The compound of claim 22 wherein each bond designated by - - - is present.

24. The compound of claim 22 wherein n is 0.
25. The compound of claim 22 wherein n is 1.
26. The compound of claim 22 wherein n is 2.
27. The compound of claim 22 wherein n is 3.

28. The compound of claim 11 wherein $R_2$ is of the formula,

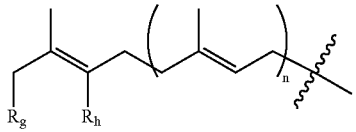

wherein:
  n is 0, 1, 2, or 3; and
  $R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

29. The compound of claim 12 wherein $R_2$ is of the formula,

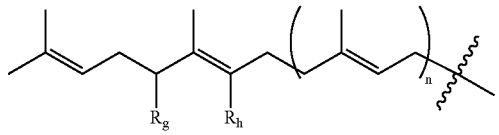

wherein:
n is 0, 1, or 2; and
$R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

30. The compound of claim 13 wherein $R_2$ is of the formula,

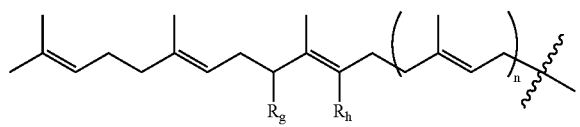

wherein:
n is 0 or 1; and
$R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

31. The compound of claim 14 wherein $R_2$ is of the formula,

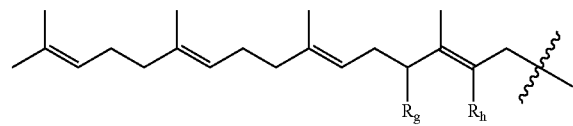

wherein:
$R_g$ and $R_h$ together with the atoms to which they are attached form an aryl ring that is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

32. The compound of claim 15 wherein $R_2$ is a saturated or unsaturated $(C_5-C_{20})$alkyl chain terminally substituted with $OR_a$ or $NR_bR_c$; wherein $R_a$ is aryl; and each $R_b$, and $R_c$ is independently H, $(C_1-C_6)$alkyl, or aryl; wherein any aryl is optionally substituted with one or more carboxy or $S(O)_2NR_dR_e$, wherein each $R_d$ and $R_e$ is independently H or $(C_1-C_6)$alkyl.

33. The compound of claim 32 wherein $R_2$ is of the formula,

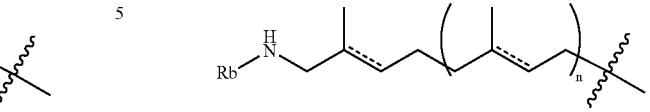

wherein:
n is 0, 1, 2, or 3;
each bond designated by - - - is independently either present or is absent; and
$R_b$ is phenyl or naphthyl and is optionally substituted with one or more carboxy or $S(O)_2NR_dR_e$, wherein each $R_d$ and $R_e$ is independently H or $(C_1-C_6)$alkyl.

34. The compound of claim 33 wherein each bond designated by - - - is present.

35. The compound of claim 6 wherein each $R_3$, $R_4$, $R_5$, and $R_6$ is OH.

36. A compound of formula I:

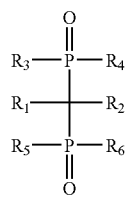

wherein:
$R_1$ is an unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;
$R_2$ is a saturated or unsaturated $(C_5-C_{20})$alkyl chain that optionally comprises one or more aryl rings in the chain and that is optionally substituted with one or more halo, trifluoromethyl, $-OR_a$, $-P(=O)(OR_a)_2$, or $-NR_bR_c$;
each $R_3$, $R_4$, $R_5$, and $R_6$ is $(C_1-C_6)$alkoxy;
each $R_a$ is independently H, $(C_1-C_6)$alkyl, or aryl; and
each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;
wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl;
or a pharmaceutically acceptable salt or prodrug thereof.

37. The compound of claim 35 which is a prodrug.

38. The prodrug of claim 37 wherein one or more of $R_3$, $R_4$, $R_5$, and $R_6$ is a group that is cleaved in vivo to provide a corresponding compound wherein said one or more of $R_3$, $R_4$, $R_5$, and $R_6$ is OH.

39. The prodrug of claim 38 wherein one or more of $R_3$, $R_4$, $R_5$, and $R_6$ is pivaloyloxymethyloxy, s-acyl-2-thioethyloxy, or an amino acid.

40. A compound as described in claim 1 that comprises or that is linked to one or more detectable groups.

41. The compound of claim 40, wherein at least one of the one or more detectable groups is a fluorescent group.

42. The compound of claim 40, wherein at least one of the one or more detectable groups is a radionuclide.

43. A pharmaceutical composition comprising a compound as described in claim 1 and a pharmaceutically acceptable carrier.

44. A compound as described in claim 4 that comprises or that is linked to one or more detectable groups.

45. The compound of claim 44, wherein at least one of the one or more detectable groups is a fluorescent group.

46. The compound of claim 44, wherein at least one of the one or more detectable groups is a radionuclide.

47. A pharmaceutical composition comprising a compound as described in claim 4 and a pharmaceutically acceptable carrier.

48. A compound as described in claim 6 that comprises or that is linked to one or more detectable groups.

49. The compound of claim 48, wherein at least one of the one or more detectable groups is a fluorescent group.

50. The compound of claim 48, wherein at least one of the one or more detectable groups is a radionuclide.

51. A pharmaceutical composition comprising a compound as described in claim 6 and a pharmaceutically acceptable carrier.

52. A compound as described in claim 15 that comprises or that is linked to one or more detectable groups.

53. The compound of claim 52, wherein at least one of the one or more detectable groups is a fluorescent group.

54. The compound of claim 52, wherein at least one of the one or more detectable groups is a radionuclide.

55. A pharmaceutical composition comprising a compound as described in claim 15 and a pharmaceutically acceptable carrier.

56. The compound tetramethyl (E)-1,1-bis(4,8-dimethyl-nona-3,7-dienyl)-1,1-bisphosphonate; tetraethyl 4,8-dimethyl-3,7-nonadienyl-1,1-bisphosphonate; tetraethyl (2E, 6E)-1-(3-methyl-but-2-enyl)-3,7,11-trimethyl-dodeca-2,6,10-trienyl-1,1-bisphosphonate; 1-(3,7-dimethyl-octa-2,6-dienyl)-4,8-dimethyl-nona-3,7-dienyl-1,1-bisphosphonic; acid or a salt thereof; tetrapivaloyloxymethyl (E)-1,1-bis(4, 8-dimethyl-nona-3,7-dienyl)-1,1-bisphosphonate; (2E,6E)-1-(3-methyl-but-2-enyl)-3,7,11-trimethyl-dodeca-2,6,10-triene-1,1-bisphosphonate or a salt thereof; or a compound of the following formula:

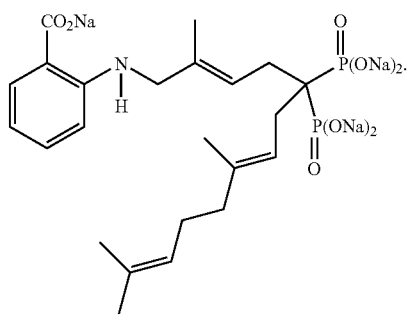

57. A pharmaceutical composition comprising a compound as described in claim 56 and a pharmaceutically acceptable carrier.

\* \* \* \* \*